US008323706B2

(12) United States Patent
Cleveland et al.

(10) Patent No.: US 8,323,706 B2
(45) Date of Patent: Dec. 4, 2012

(54) ANTIESTROGENIC GLYCEOLLINS SUPPRESS HUMAN BREAST AND OVARIAN CARCINOMA PROLIFERATION AND TUMORIGENESIS

(75) Inventors: Thomas E. Cleveland, Mandeville, LA (US); Stephen M. Boue, New Orleans, LA (US); Matthew E. Burow, Slidell, LA (US); John A. McLachlan, New Orleans, LA (US)

(73) Assignees: The United States of America, as represented by the Secretary of Agriculture, Washington, DC (US); Tulane Educational Fund, New Orleans, LA (US)

( * ) Notice: Subject to any disclaimer, the term of this patent is extended or adjusted under 35 U.S.C. 154(b) by 151 days.

(21) Appl. No.: 12/082,583

(22) Filed: Apr. 11, 2008

(65) Prior Publication Data
US 2008/0200537 A1    Aug. 21, 2008

Related U.S. Application Data

(62) Division of application No. 11/118,431, filed on Apr. 29, 2005, now abandoned.

(51) Int. Cl.
*A61K 36/00* (2006.01)
*A61K 36/48* (2006.01)
(52) U.S. Cl. .................................. 424/725; 424/757
(58) Field of Classification Search .................. None
See application file for complete search history.

(56) References Cited

U.S. PATENT DOCUMENTS
6,855,350 B2 * 2/2005 Lu .................. 424/757

OTHER PUBLICATIONS

Burow et al. (Phytochemical Glyceollins, Isolated from Soy, Mediate Antihormonal Effects through Estrogen Receptor, Journal of Clinical Endocrinology & Metabolism vol. 86, No. 4 pp. 1750-1758, copyrighted 2001).*
Kornblith et al. (In Vitro response of Ovarian Cancers to Platinums and Taxanes, Anticancer Research 23: 543-548 (2003)).*
Bhattacharyya et al. (Differential sensitivity of Phytophthora magasperma f.sp. glycinea isolated to glyceollin isomers, Physiological Plant Pathology, (1985), vol. 27 No. 3, pp. 299-310).*

Burow, Matthew E., et al., "Phytochemical Glyceollins, Isolated from Soy, Mediate Antihormonal Effects through Estrogen Receptor α and β", *J. of Clinical Endocrinology & Metabolism*, vol. 86, (4), pp. 1750-1758, 2001.
Constantinou, Andreas I., et al., "Genistein Induces Maturation of Cultured Human Breast Cancer Cells and Prevents Tumor Growth in Nude Mice", *Am J. Clin. Nutr.*, vol. 68, pp. 1426S-1430S, 1998.
Diel, Patrick, et al., "Phytoestrogens and Carcinogenesis Differential Effects of Genistein in Experimental Models of Normal and Malignant Rat Endometrium", *Human Reproduction*, vol. 15, (5), pp. 997-1006, May 2001.
Stygar, Denis, et al., "Effects of SERM (selective estrogen receptor modulator) treatment on growth and proliferation in rat uterus", *Reproductive Biology and Endocrinology*, vol. 1, 40, pp. 1-8, May 2003.

* cited by examiner

*Primary Examiner* — Terry McKelvey
*Assistant Examiner* — Randall Winston
(74) *Attorney, Agent, or Firm* — John D. Fado; Evelyn M. Rabin (57) ABSTRACT

The flavonoid family of phytochemicals, particularly those derived from soy, has received attention regarding their hormonal activity and their effects on human health and disease. The types and amounts of these compounds in soy and other plants are controlled by both constitutive expression and stress-induced biosynthesis. The health benefits of soy may therefore be dependent upon the amounts of the various hormonally active phytochemicals present. We have identified increased biosynthesis of the isoflavonoid phytoalexin compounds, Glyceollins I, II and III, in soy plants grown under stressed conditions (elicited soy), which exhibit marked antiestrogenic effects on ER function. Here we demonstrate that specific glyceollins, isolated from elicited soy, displayed antiestrogenic activity, suppressing basal and estrogen stimulated colony formation of ER-positive estrogen dependent breast cancer cells and inhibiting ER-dependent gene expression of progesterone receptor (PgR) and stromal derived factor-1 (SDF1/CXCL12). Examining the effects of glyceollin on in vivo tumor formation/growth we demonstrate the ability of glyceollins to significantly suppress basal and estrogen-stimulated tumor growth of ER-positive MCF-7 breast and BG-1 ovarian carcinoma cells in ovariectomized female nude mice. We further demonstrate that the effects of glyceollins on suppression of tumor growth correlate with inhibition of estrogen stimulated PgR expression. In contrast to the uterotropic activity of tamoxifen the glyceollins displayed no uterine agonist activity. The Glyceollin (I-III) compounds may represent an important component of the health effects of soy as well as represent novel anti-estrogens useful in the prevention or treatment of breast and ovarian carcinoma.

1 Claim, 8 Drawing Sheets

FIG. 8

# ANTIESTROGENIC GLYCEOLLINS SUPPRESS HUMAN BREAST AND OVARIAN CARCINOMA PROLIFERATION AND TUMORIGENESIS

This application is a divisional application of application Ser. No. 11/118,431, filed Apr. 29, 2005, now abandoned, which is herein incorporated by reference in its entirety.

BACKGROUND OF THE INVENTION

1. Field of the Invention

The present invention relates to increased biosynthesis and isolation of the isoflavonoid phytoalexin compounds, Glyceollins I, II and III, in soy plants grown under stressed conditions, a composition containing said glyceollin(s), a selective estrogen receptor modulator, and a method of treating and preventing breast and ovarian carcinoma while inhibiting selective estrogen receptor modulator-induced uterotrophic effects.

2. Description of the Relevant Art

During endocrine therapy, the antiestrogen tamoxifen has been shown to prevent pre- and postmenopausal breast cancer and to be a beneficial adjuvant therapy for women with estrogen receptor-positive tumors. Ultimately tumors can develop resistance, and in the case of the antiestrogen tamoxifen, tamoxifen can increase the risk of endometrial cancer (Brown, K. 2002. *Expert Opin. Drug Saf.* 1: 253-267). Consequently, efforts have been made to develop new antiestrogens from both synthetic and natural sources. Many naturally occurring agents, particularly flavonoids, have shown chemopreventive and anticancer potential in a variety of in vitro and in vivo models (Diel et al. 2001. *Human Reproduction* 16(5): 997-1006; Barnes, S. 1997. *Breast Cancer Res. Treat.* 46: 169-179; Aronson et al. 1999. *Nutr. Cancer* 35(2): 130-136). The isoflavone genistein has received much attention over the last few years as a potential anticancer agent due to its wide-range effects on a number of cellular processes. The chemopreventive effects of genistein and other flavonoids have spurred research to discover other naturally occurring flavonoids in soybean and other plants with anticancer activities.

Phytoalexins constitute a chemically heterogeneous group of substances belonging to the various sub-classifications of flavonoids. Phytoalexins are low molecular weight antimicrobial compounds that are synthesized de novo and accumulate in plants as a stress response (Darvill et al. 1984. *Ann. Rev. Plant Physiol.* 35: 243-275; Paxton, J. D. 1991. In: *Emerging Problems Resulting from Microbial Contamination*, Sharma et al. (Eds.), CRC Press, Boca Raton, Fla.). The phytoalexins are products of a plant's secondary metabolism, and often accumulate at infection sites at concentrations that inhibit fungal and bacterial growth (Darvill et al., supra; Paxton, J. D., supra). Countless stress factors or physical stimuli induce phytoalexin accumulation including freezing, ultraviolet light exposure and exposure to microorganisms. In addition, compounds referred to as elicitors, either abiotic or biotic, can stimulate the biosynthesis of phytoalexins. Given that the biosynthesis of isoflavonoids, particularly phytoalexins, can be regulated by external factors, the type and amount of hormonally active phytochemicals may vary form source to source. In soybean, several phytoalexins, particularly the glyceollins, are produced under conditions of stress. The glyceollins (mixture of Glyceollin I, II, and III) have been produced in high concentrations using several elicitors and have antimicrobial activity against several plant pathogens (Darvill et al., supra; Graham et al. 1990. *Mol. Plant-Microbe Interactions* 3(3): 157-166; Daniel et al. 1999. *Environ. Health Perspectives* 107: 109-114; Rivera-Vargas et al. 1993. *Phytochem.* 32 (4): 851-857; Rizk et al. 1984. *Qual. Plant Foods Human Nutr.* 34 (3): 203-210; Bhattacharyya et al. 1986. *Physiol and Mol. Pl. Pathol.* 29: 227-237; Graham et al. 1991. *Mol. Plant-Microbe Interactions* 4(1): 60-68).

Studies linking consumption of a phytochemical rich diet to a decreased risk of hormone-dependent tumors such as breast cancer suggest a role for these compounds in prevention or suppression of cancer. In regards to soy rich diets, the two major phytochemicals present are the isoflavones genistein and daidzein, which exist in the aglycone or conjugated form. Studies support the view that isoflavones may have protective effects with regard to estrogen-dependent cancer, particularly breast cancer. A role for isoflavones in the chemoprevention or potential treatment of breast carcinoma has been studied (Constantinou et al. 1998. *Am. J. Clin. Nutr.* 68 (6 Suppl.): 1426S-1430S; Hewitt et al. 2003. *Cancer Lett.* 192 (2): 133-143). Several animal studies suggest that isoflavones retard cancer development. Newborn female rats treated neonatally with genistein and then exposed to a carcinogen had increased latency and decreased incidence and multiplicity of mammary tumors compared with vehicle-treated animals (Lamartiniere et al. 1995a. *Carcinogenesis* 16(11): 2833-2840; Lamartiniere et al. 1995b. *Proc. Soc. Exp. Biol. Med.* 208 (1): 120-123).

However, studies examining dietary genistein effects on estrogen-responsive human breast carcinoma cells implanted into mice suggest the agonist activity of genistein may enhance tumor growth (Barnes, supra). These animal studies using isolated isoflavones have yielded contradictory results as to the effects of these on tumor growth and chemoprevention suggesting a complex role for the effects of flavonoids on cancer cells. The effects of estrogenic compounds such as daidzein or genistein on breast cancer cell proliferation and tumorigenesis may therefore be in part complicated by a complex activity of both agonistic effects on estrogen receptor (ER) function along with tyrosine kinase inhibitory activity at higher doses.

Soybeans grown under stressed conditions were examined to determine if additional unidentified compounds isolated from soybean could further elucidate the role of phytochemicals in breast cancer tumorigenesis and estrogen receptor function. Through these studies, we described the isolation of the glyceollins as a mixture of three isomers (Glyceollin I, II, and III) from stressed soybeans. Functional analysis of these compounds demonstrated that the glyceollins displayed a marked antiestrogenic effect on estrogen receptor signaling; direct binding to the estrogen receptor correlated with a comparable suppression of 17β-estradiol (E2)-induced proliferation in MCF-7 cells (Burow et al. 2001. *J. Endocrinol.* 86 (4): 1750-1758). Furthermore, in contrast to other isoflavones found in soy, no estrogenic activity was observed with the glyceollins in vitro. From these studies, we hypothesized that the glyceollins represented novel antiestrogenic flavonoids naturally produced by soy that may be relevant to human health.

There is a need to develop new antiestrogens from both synthetic and natural sources. Further, there is a need to reduce the risks of estrogenic effects as has been observed with tamoxifen in uterine tissue. Thus, in view of the antiestrogenic activity of the glyceollins in vitro and its lack of estrogenic activity, the efficacy of the glyceollins as a novel therapy in vivo was determined.

SUMMARY OF THE INVENTION

We have isolated glyceollins from elicited soy and discovered that glyceollins are novel antiestrogens useful in the prevention and treatment of breast and ovarian carcinoma.

In accordance with this discovery, it is an object of the invention to provide isolated glyceollins (Glyceollin I, II, and III) from elicited soy.

It is a further object of the invention to provide a composition containing glyceollin for preventing or minimizing the development or growth of breast cancer and ovarian cancer.

It is another object of the invention to provide a method for preventing or minimizing the development or growth of breast cancer and ovarian cancer in a mammal, particularly a human.

Also part of this invention is a kit, comprising a glyceollin-containing composition for preventing or minimizing the development or growth of breast cancer and ovarian cancer.

Other objects and advantages of this invention will become readily apparent from the ensuing description.

BRIEF DESCRIPTION OF THE DRAWINGS

FIGS. 7A-C depict glyceollin effects on uterine morphology in nu/nu mice. FIG. 7A depicts the effects of glyceollin on uterine area, FIG. 7B, on uterine diameter, and FIG. 7C, on uterine epithelial height. E2 significantly increased uterine size and epithelial height, while glyceollin-alone had no effect on any of the measures. Uterine area and diameter were significantly lower for E2+glyceollin compared to E2 alone. Treatments included 4-5 animals per group. Histomorphometric measures were quantitated from H&E-stained slides. Different letters indicate significant differences between groups ($p<0.05$ by ANOVA).

DETAILED DESCRIPTION OF THE INVENTION

This invention describes the increased biosynthesis of the isoflavonoid phytoalexin compounds, Glyceollins I, II and III, in soy plants grown under stressed conditions (elicited soy) and their marked antiestrogenic effects on estrogen receptor function. To fully understand the role of glyceollins' anti-estrogenic and anti-cancer properties, we used the well-established model of MCF-7 and BG-1 tumor formation in immunocompromised female ovariectomized nu/nu mice to examine the effects of glyceollins on both basal and estrogen-stimulated growth of xenografted tumor cells. In this model, using the ER-positive and estrogen-dependent MCF-7 breast and BG-1 ovarian carcinoma cell lines, the in vivo antiestrogenic activity of the glyceollins has been established.

As used herein, the term "ER" refers to "estrogen receptor". The terms "breast cancer" and "breast carcinoma" refer to any cancer having its origin in breast cells, and includes metastatic and local forms of breast cancer (node negative and node positive), as well as ER positive and ER negative forms of breast cancer. The terms "ovarian cancer" and "ovarian carcinoma" refer to all stages of ovarian cancer and includes metastatic and local forms of ovarian cancer, as well as ER positive and ER negative forms of ovarian cancer. The terms "estrogenic effects observed in uterine tissue" and "uterotrophic effect" means the increase in uterine size that can be secondary to proliferation of uterine epithelial cells, which frequently is a side effect of administration of selective estrogen receptor modulators to women, and which appears to be directly related to development of endometrial cancer. The term "minimize" or "reduce", or a derivative thereof, includes a complete or partial inhibition of a specified biological effect (which is apparent from the context in which the term minimize is used). The term "glyceollin" may mean both a single glyceollin and plural glyceollins when the glyceollin is defined as at least one of a selected group of glyceollins. "SERM" means a selective estrogen receptor modulator and its physiologically acceptable salts, other than tamoxifen, which is a compound which produces estrogen antagonist effects in one or more desired target tissues (e.g. breast tissue and uterine tissue), while producing either estrogen agonist effects or minimal agonism in other non-target tissues. "Tamoxifen" refers to the clinically utilized antiestrogen.

The glyceollin compounds used in the compositions and methods of the present invention are naturally occurring substances which may be found in plants such as soybeans that are stressed or that have been treated with elicitors. The glyceollin compounds may be isolated from the plant sources in which they naturally occur after treatment with an elicitor, or may be synthetically prepared by processes known in the art.

It is preferred to extract the glyceollins useful in the compositions and methods of the present invention from the plant materials in which they naturally occur. A preferred method of isolating the glyceollin compounds is to extract the plant materials with an alcohol, preferably methanol or ethanol, or an aqueous methanolic solution, to remove the glyceollins from the plant material. It is preferred to comminute the plant material before extracting the glyceollin compounds to maximize recovery of glyceollin compounds from the plant material. The glyceollin compounds are isolated from the extract by conventional separation procedures, such as high performance liquid chromatography, HPLC.

In a preferred embodiment, the glyceollin compounds are isolated from a soy material. Soy materials from which the glyceollin compounds can be isolated include elicitor-treated: soy seeds, soybeans, dehulled soybeans, soy cotyledons, soy leaf tissue, soy roots, and soy hypocotyls. In one embodiment, the glyceollins are extracted from soy seeds, with a low molecular weight organic extractant, preferably an alcohol, ethyl acetate, acetone, or ether, and most preferably aqueous ethyl alcohol or methyl alcohol Here we demonstrate that specific glyceollins, isolated from elicited soy, displayed antiestrogenic activity, significantly suppressing basal and estrogen-stimulated colony formation of ER-positive estrogen dependent breast cancer cells and inhibiting ER-dependent gene expression of progesterone receptor (PgR) and stromal derived factor-1 (SDF1/CXCL12). Glyceollins inhibited the growth of human ER-positive breast cancer (MCF-7) and ovarian cancer (BG-1) cells injected subcutaneously in female athymic ovariectomized nude mice.

The MCF-7 and BG-1 cancer-cell lines are fully estrogen-dependent for growth in ovariectomized nude mice. The glyceollins displayed little estrogenic activity in bioassays, and the in vitro antiestrogenic activity observed at 10 µM provided evidence for inhibition of estrogen-dependent human breast and ovarian carcinomas xenografted into immunoincompetent (nude) mice. Glyceollins injected subcutaneously with 17β-estradiol significantly reduced MCF-7 and BG-1 tumor volumes compared to control groups with estradiol only. At day 20 in Glyceollin treatments with added 17β-estradiol, MCF-7 tumor volume was reduced 53.4%, and BG-1 tumor volume was reduced 73.1% (See Example 5). The ability of Glyceollins to also suppress PgR expression in MCF-7 BG-1 cells further exemplifies the antiestrogenic activity of these compounds. Thus, our earlier studies showing the ability of the glyceollins to antagonize the effects of 17β-estradiol in vitro are also observed for breast and ovarian cancer models in vivo.

The uterotrophic assay that utilizes estrogen-induced growth of the uterus in ovariectomized mice is one of the principal assays used to evaluate the estrogenic and antiestrogenic properties of isoflavones. Several isoflavones, including genistein, have demonstrated agonist activity in the uterine (Whitten et al. 1994. Steroids 59: 443-449; Diel et al., supra). In these same animals treated for 20 days with vehicle, estradiol, glyceollin or estrogen+glyceollin, uterine size and morphology was examined. In the present study, the glyceollins alone showed no agonist uterotrophic activity. However, glyceollin treatment antagonized the 17β-estradiol effects on the uterus, significantly reducing uterine area and diameter, but non-significantly reduced overall uterine fixed weight. The ability of the glyceollins to function as an estrogen antagonist in the uteri in mice is a distinct advantage when compared to other phytoestrogens and tamoxifen. In several studies tamoxifen has increased uterine weight and acts as an agonist in the uteri (Stygar et al. 2003. *Reprod. Biol. Endocrinol.* 1: 40-47; Nunez et al. 2004. *Clin. Cancer Res.* 10: 5375-5380). In comparison, the ability of tamoxifen alone to increase uterine fixed weight over control was not observed with glyceollins at 20 days. These results suggest that the glyceollins may be functioning as phyto-SERMs (Selective Estrogen Receptor Modulators) selectively antagonizing ER function in a tissue-type specific manner. Our data indicate that glyceollins in vivo inhibit the growth of human breast and ovarian cancer xenografts and function as phyto-SERMs, antagonizing breast and uterine epithelial proliferation.

The present invention is a composition useful for preventing or minimizing the development or growth of breast and ovarian cancer. The composition contains glyceollins, selective estrogen receptor modulators. The glyceollin-containing material necessary to form compositions in accordance with the present invention may be obtained as described above. The composition contains from about 1% to about 99% glyceollin, by weight of biologically active ingredients.

The glyceollin is present in the composition in an amount sufficient to prevent, minimize, or reverse the development or growth of breast cancer and/or ovarian cancer in a woman. Preferably at least glyceollin is present at a concentration of 100 nM in the composition, more preferably at a concentration from about 100 nM to about 50 µM. In a most preferred embodiment, the glyceollin is present in the composition in an amount sufficient to prevent, minimize, or reverse the development or growth of breast cancer and/or ovarian cancer by itself.

In another preferred embodiment, the glyceollin is present in the composition in an amount sufficient to prevent or minimize the composition's SERM-induced uterotrophic effects when the composition is administered to a woman. The glyceollin should be present in a ratio of glyceollin:SERM of from about 0.25:1 to about 100:1 by weight, and more preferably from about 0.5:1 to about 50:1 by weight, to be present in the composition in an amount sufficient to prevent or minimize the composition's SERM induced uterotrophic effects. In a most preferred embodiment, the glyceollin is present in the composition in an amount sufficient to augment the composition's SERM-induced prevention or minimization of the development or growth of breast cancer and/or ovarian cancer and to prevent or minimize the composition's SERM-induced uterotrophic effects when the composition is administered to a woman.

A composition in accordance with the present invention containing a SERM and glyceollin(s) can be prepared by conventional procedures for blending and mixing compounds. Preferably, the composition also includes an excipient, most preferably a pharmaceutical excipient. Compositions containing an excipient and incorporating the SERM and glyceollin can be prepared by procedures known in the art. For example, the glyceollin, or the composition containing SERM and the glyceollin, can be formulated into tablets, capsules, powders, suspensions, solutions for oral administration and solutions for parenteral administration including intravenous, intradermal, intramuscular, and subcutaneous administration, and into solutions for application onto patches for transdermal application with common and conventional carriers, binders, diluents, and excipients.

Inert pharmaceutically acceptable carriers useful to form pharmaceutical compositions in accordance with the present invention include starch, mannitol, calcium sulfate, dicalcium phosphate, magnesium stearate, silicic derivatives, and/or sugars such as sucrose, lactose, and glucose. Binding agents include carboxymethyl cellulose and other cellulose derivatives, gelatin, natural and synthetic gums including alginates such as sodium alginate, polyethylene glycol, waxes and the like. Diluents useful in the invention include a suitable oil, saline, sugar solutions such as aqueous dextrose or aqueous glucose, DMSO, and glycols such as polyethylene or polypropylene glycol. Other excipients include lubricants such as sodium oleate, sodium acetate, sodium stearate, sodium chloride, sodium benzoate, talc, and magnesium stearate, and the like; disintegrating agents including agar, calcium carbonate, sodium bicarbonate, starch, xanthan gum, and the like; and adsorptive carriers such as bentonite and kaolin. Coloring and flavoring agents may also be added to the pharmaceutical compositions.

EXAMPLES

Having now generally described this invention, the same will be better understood by reference to certain specific examples, which are included herein only to further illustrate the invention and are not intended to limit the scope of the invention as defined by the claims.

Example 1

Soybean Treatment and Harvesting

*Aspergillus sojae* (SRRC 1125) cultures were grown at 25° C. in the dark on potato dextrose agar. After 5 days, inoculum was prepared by harvesting conidia ($3.4 \times 10^7$/ml) in 15 ml sterile, distilled $H_2O$. Seeds from commercial soybean variety Asgrow 5902 were surface-sterilized for 3 min in 70% ethanol followed by a quick deionized-$H_2O$ rinse and two 2 min rinses in deionized-$H_2O$. Seeds were presoaked in sterile deionized-$H_2O$ for 4-5 hr, then chopped for 2 min in a Cuisinart food processor. *A. sojae* spore suspension (300 µl) was applied to the cut surface of seeds on each tray. All trays were stored at 25° C. in the dark for three days, rinsed with water to remove spores, and oven dried at 40° C. for 24 hrs. Seeds were ground using a Waring blender before extraction.

Example 2

Isolation of Glyceollins

Figure 1:
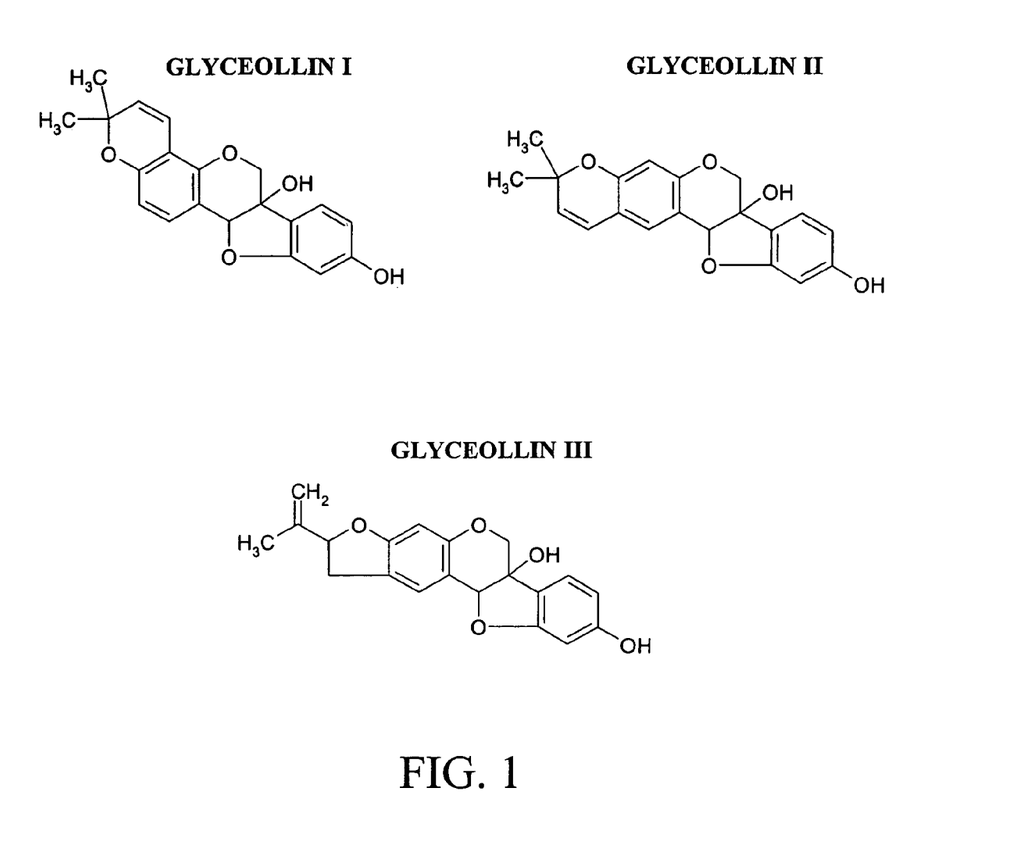
FIG. 1 depicts the structures of Glyceollins I, II, and III.

A mixture of Glyceollins I, II, and III were isolated using a procedure developed at the Southern Regional Research Center (ARS, USDA, New Orleans, La.). Soybean seeds (1 kg) were sliced and inoculated with *Aspergillus sojae*, as in Example 1. After three days, the glyceollins were extracted from the inoculated seeds with methanol (1 liter). The Glyceollins were isolated using preparative scale HPLC using two Waters 25 mm 10 µm particle size µBondapak $C_{18}$ radial compression column segments combined using an extension tube. HPLC was performed on a Waters 600E System Controller combined with a Waters UV-VIS 996 detector. Elution was carried out at a flow rate of 8.0 ml/min with the following solvent system: A+acetonitrile, B=water; 5% A for 10 min, then 5% A to 90% A in 60 min followed by holding at 90% A for 20 min. The injection volume was 20 ml. The fraction containing the glyceollins was concentrated under vacuum and freeze-dried. The glyceollins were confirmed by UV-VIS spectrophotometry. A mixture of Glyceollins I (68%), II (21%), and III (11%) (FIG. 1) were isolated and used in animal testing. The solvents acetonitrile (HPLC grade) and methanol were purchased from Aldrich Chemical Company. Water was obtained using a Millipore system and used during sample preparation procedures and HPLC analyses.

Example 3

Cell Culture

In Vitro Colony Assay

The MCF-7N cell variant is a subclone of MCF-7 cells from the American Type Culture Collection (Manassas, Va.) that was generously provided by Louise Nutter (University of Minnesota, Minneapolis, Minn.) and has been previously described (Graham et al., supra). The BG-1 cell line has been previously described. MCF-7 and BG-1 cells were grown in Dulbecco's modified minimal medium (pH 7.4; Life Technologies, Inc., Grand Island, N.Y.) supplemented with 10% fetal bovine serum (Hyclone, Salt Lake City, Utah). For studies with estrogen, the cells were cultured in medium supplemented with 5% charcoal-stripped fetal bovine serum. The cells were incubated at 37° C. in an atmosphere of 5% $CO_2$ and air.

MCF-7 cells are plated at $10^3$/well in 6 well Cluster dishes, and incubated overnight. Cells are cultured and treated in DMEM without phenol red; phenol red interacts with estrogen receptors. Treatment and control plates were incubated at 37° C., 5% $CO_2$. Plates were observed periodically. When colonies were of a size of 50 cells or more, at Day 14, cells were fixed with glutaraldehyde for 30 min at 37° C., washed, and stained with Crystal violet (0.4%) for 1 hr. Colonies were counted manually. This method is used to study the effects of chemical or physical agents on cell survival and proliferation; 1 colony=1 cell.

Figure 2:
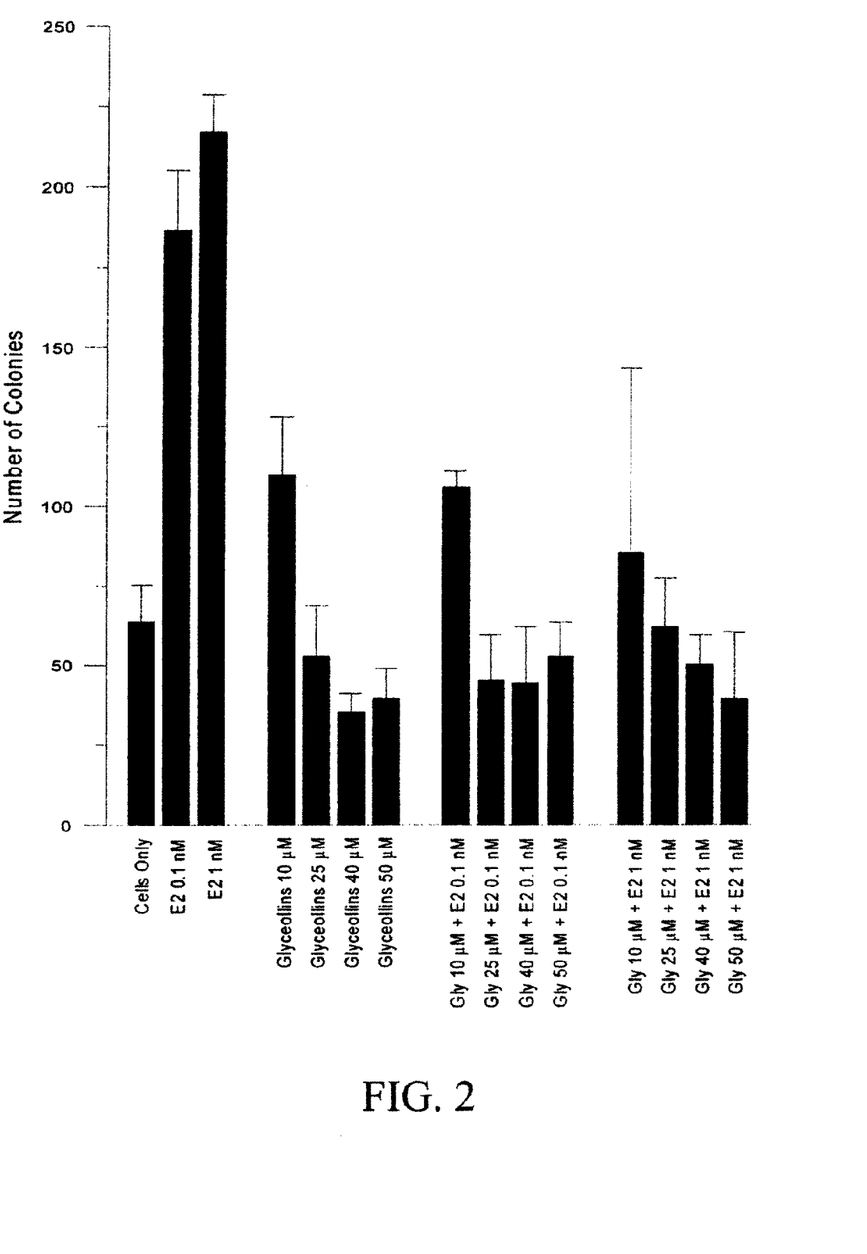
FIG. 2 shows the effects of glyceollins in the in vitro MCF-7 colony assay.

The antiestrogenic activity of a mixture of Glyceollins (I, II, and III shown in FIG. 1) was previously described using a combination of in vitro assays (Burow et al., supra). Analysis of this mixture by HPLC revealed a relative percentage composition of Glyceollin I (68%), Glyceollin II (21%) and Glyceollin III (11%) in this mixture. A clonogenicity assay was used to examine the effects of a mixture of Glyceollins on MCF-7 breast carcinoma cell proliferation and survival (FIG. 2). As expected, treatment of MCF-7 cells with estrogen enhanced colony formation. Estradiol-stimulated growth of MCF-7 cells was reduced in a dose-dependent manner in experiments in which cells were treated with estradiol (1 nM) together with glyceollin at doses ranging from 10 µM to 50 µM. Glyceollins together with a lower concentration of estradiol (0.1 nM) also reduced MCF-7 growth. Treatment with increasing concentrations of Glyceollin I-III reduced both basal- (vehicle-) induced colony formation as well as estrogen-stimulated clonogenicity. An increase in colony formation above control levels was observed when using the glyceollins at 10 µM.

Example 4

Treatment Protocols

Immune compromised (nu/nu) female, ovariectomized mice (29-32 days old) were obtained from Charles-River Laboratories (Wilmington, Mass.). The animals were allowed a period of adaptation in a sterile and pathogen-free environment. Cages, bedding, food, and water were autoclaved before use. Animals were housed five per cage and received phytoestrogen-free sterile food and water ad libitum. Mice received subcutaneous inoculations under anesthesia (Isofluorane and Oxigene) delivered by mask. For animals receiving estradiol, an estradiol pellet (0.72 mg, 60 day release, Innovative Research) was implanted subcutaneously in the lateral area of the neck in the middle point between the ear and shoulder using a precision trochar (10 gauge). MCF-7 and BG-1 cells in the exponential phase of growth, were harvested using PBS/EDTA solution and washed. Viable cells ($5 \times 10^6$) in a 50 µl sterile PBS suspension were mixed with 100 µl Matrigel (BD Biosciences, Bedford, Mass.). Cells in Matrigel were injected bilaterally in the mammary fat pad (MFP) through a 5 mm incision at the hypogastrium area, and the incision was closed using staples. The glyceollin mixture was suspended in a solution of DMSO (⅓ volume) and propylene glycol (⅔ volume) and was administered subcutaneously in the dorsal area at 20 mg/kg/mouse/day for 20 days starting at time of tumor implantation (Day 1). Tumor size was measured every two days using calipers. The volume of the tumor was calculated using the following formula: $\frac{4}{3}\pi LM^2$, where M is the smaller radius.

Example 5

Tumor Growth in Glyceollin Treated MCF-7 and BG-1 Xenograft Mice

Figure 3:
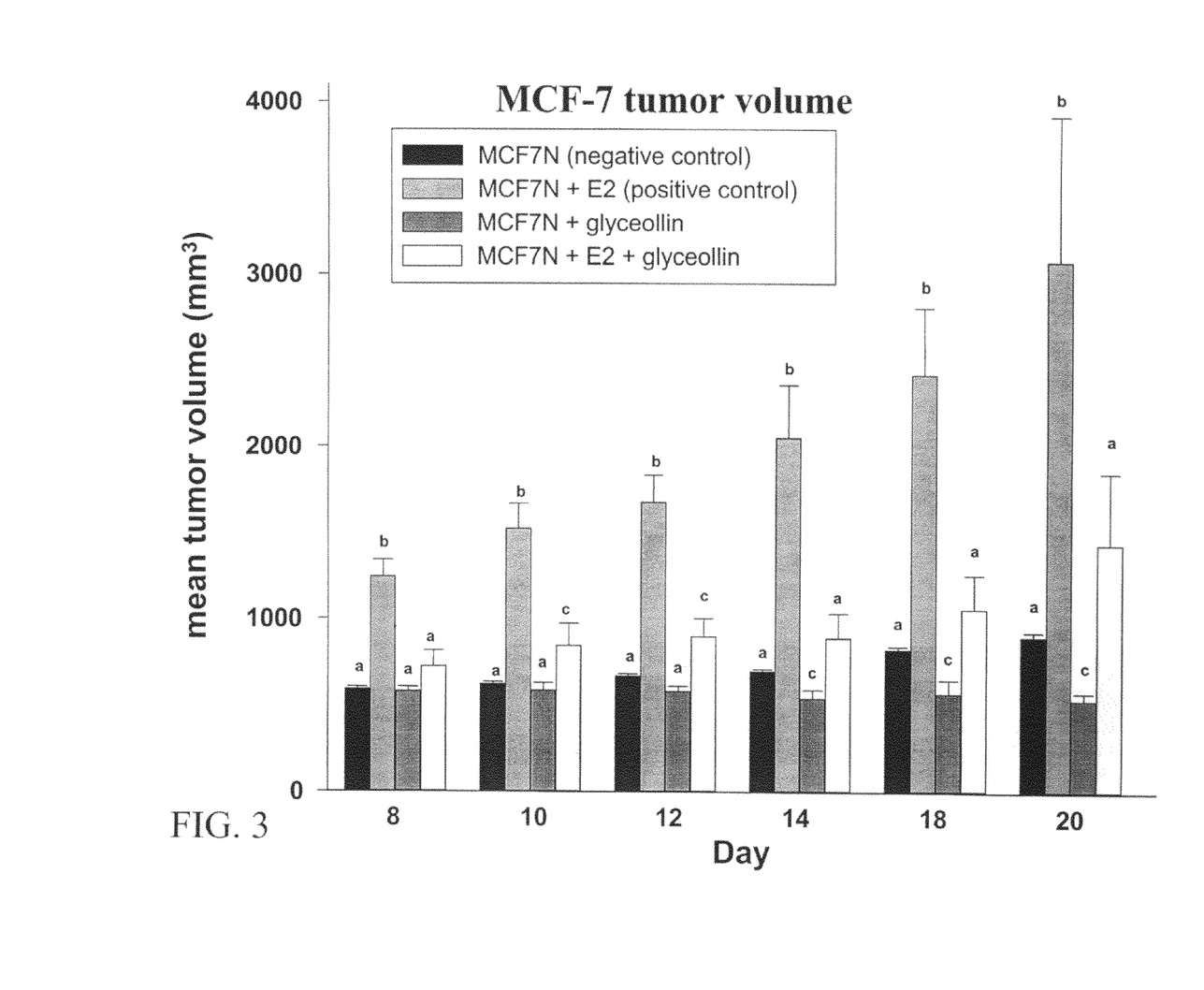
FIG. 3 depicts the effects of the glyceollins on breast tumor growth in vivo ($mm^3$, group means±SEM). MCF-7 breast carcinoma cells were implanted in the mammary fat pad of nu/nu female ovariectomized mice in the presence or absence of E2-pellet. Mice were treated with or without s.c. injection of glyceollins (20 mg/kg/animal/day) for 20 days with tumor growth monitored every other day. Treatment, trial day, and treatment by trial day interactions are statistically significant ($p<0.001$, power=1.0 by repeated measures two-way ANOVA). Different letters indicate significant differences among groups on a given treatment day (by Holm-Sidak post-hoc multiple pair-wise comparisons testing).
Figure 4:
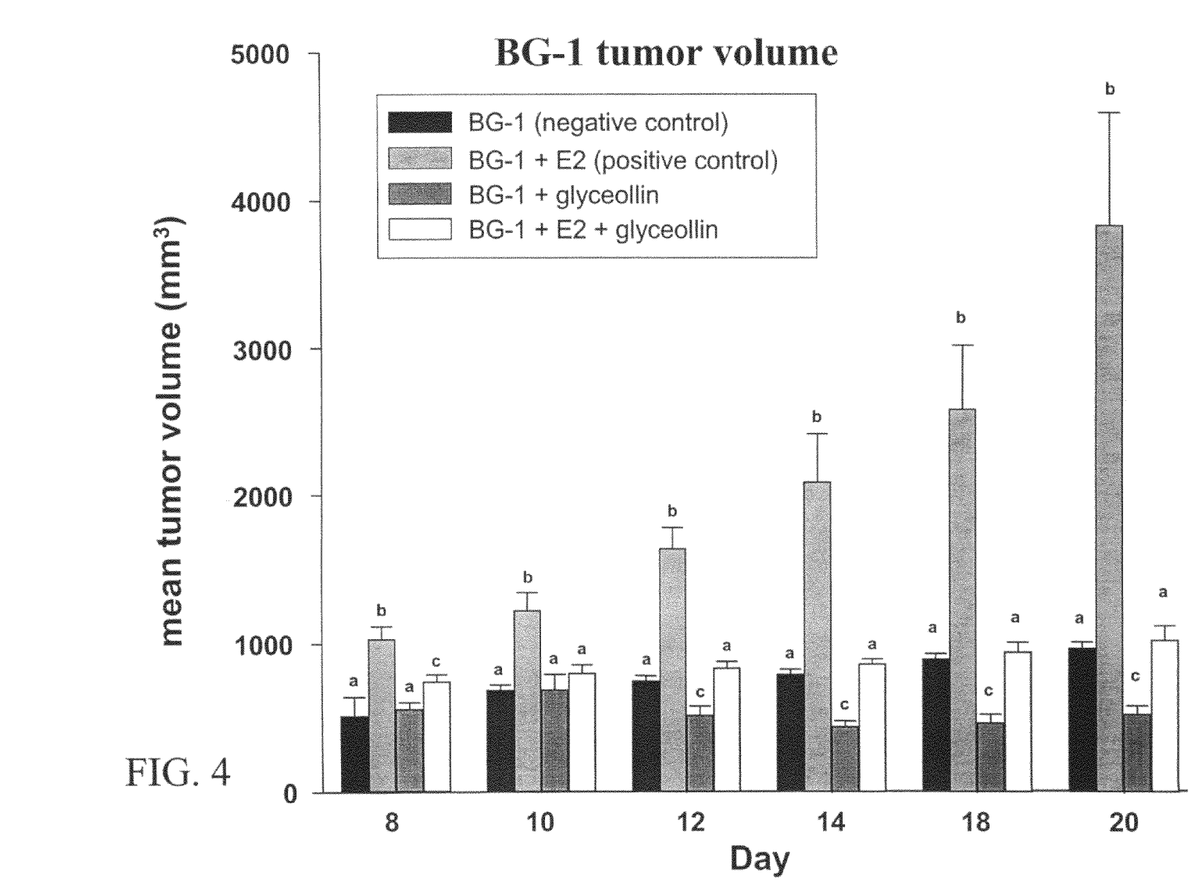
FIG. 4 shows the effects of the glyceollins on ovarian tumor growth in vivo ($mm^3$, group means±SEM). BG-1 ovarian carcinoma cells were implanted in the mammary fat pad of nu/nu female ovariectomized mice in the presence or absence of E2-pellet. Mice were treated with or without s.c. injection of glyceollins (20 mg/kg/animal/day) for 20 days with tumor growth monitored every other day. Treatment, trial day, and treatment by trial day interactions are statistically significant ($p<0.001$, power=1.0 by repeated measures two-way ANOVA). Different letters indicate significant differences among groups on a given treatment day (by Holm-Sidak post-hoc multiple pair-wise comparisons testing).

The in vivo effects of glyceollins on tumor growth formation were determined. MCF-7 or BG-1 cells were implanted into the mammary fat pad of female ovariectomized nude mice. Mice were divided into two groups: those animals implanted s.c. with estradiol pellets and those without. Tumors were implanted using Matrigel (reduced factor) to enhance tumor incidence and promote tumor growth in the presence and absence of estrogen. Glyceollins (or vehicle) were injected daily for 20 days. Measurable tumors were observed on Day 8 for both MCF-7 cells (FIG. 3) and BG-1 cells (FIG. 4). Tumors in all groups are measurable and significantly larger on Day 8 than on Day 0. Estrogen stimulated the formation of rapidly growing tumors in both MCF-7 and BG-1 implanted mice, reaching a maximal size of 3074±843 mm$^3$ in MCF-7 and 3836±756 mm$^3$ in BG-1 implanted animals by day 20 of treatment. In the negative control animals (without estrogen pellets or glyceollins), tumor incidence occurred on day 4 and tumors grew slowly with a maximal size of 899±24 mm$^3$ for MCF-7 cells and 976±42 mm$^3$ for BG-1 cells on day 20 of treatment. In the Glyceollins I-III treated groups the growth of MCF-7 and BG-1 tumors in the presence and absence of estrogen was suppressed by Glyceollins I-III treatment. Treatment with Glyceollins I-III suppressed estrogen-stimulated tumor growth. On Day 20 of treatment, glyceollin-treated animals were not significantly different from negative control levels; tumor sizes of 1433±414 mm$^3$ for MCF-7 (p=0.336) and 1031±96 mm$^3$ for BG-1 (p=0.956) were observed. In the absence of E2, Glyceollins I-III stabilized growth of tumors to 536±41 mm$^3$ in MCF-7 cells and 532±55 mm$^3$ in BG-1 tumors, thereby suppressing growth to below negative control levels. These glyceollin-treated tumors were significantly smaller than negative control tumors by day 14 for MCF-7 cells (p=0.003) and by day 12 for BG-1 cells (p=0.001). Tumors were all harvested on day 21 and sectioned for HE staining and for immunohistochemistry for Ki67 staining and progesterone receptor expression.

Example 6

Progesterone Receptor Immunochemistry

Tumor explants were resected at necropsy, fixed in 70% ethanol, embedded in paraffin, and immunostained using a primary monoclonal antibody for human progesterone receptor (PR) (NCL-PGR, Novocastra, Newcastle-upon-Tyne, UK). Staining methods included antigen-retrieval with citrate buffer (pH 6.0), biotinylated rabbit anti-mouse Fc antibody as a linking reagent, alkaline phosphatase-conjugated streptavidin as the label, and Vector Red as the chromogen (Vector Laboratories, Burlingame, Calif.). Cell staining was quantified by a computer-assisted counting technique, using a grid filter to select cells for counting (Darvill et al., supra; Burow et al., supra). At least two microscopic fields were randomly selected for each tumor and 200 cells were counted at 40× magnification. Numbers of positively stained cells were expressed as a percentage of the total number examined. All measurements were made blinded to treatment group.

Figure 5:
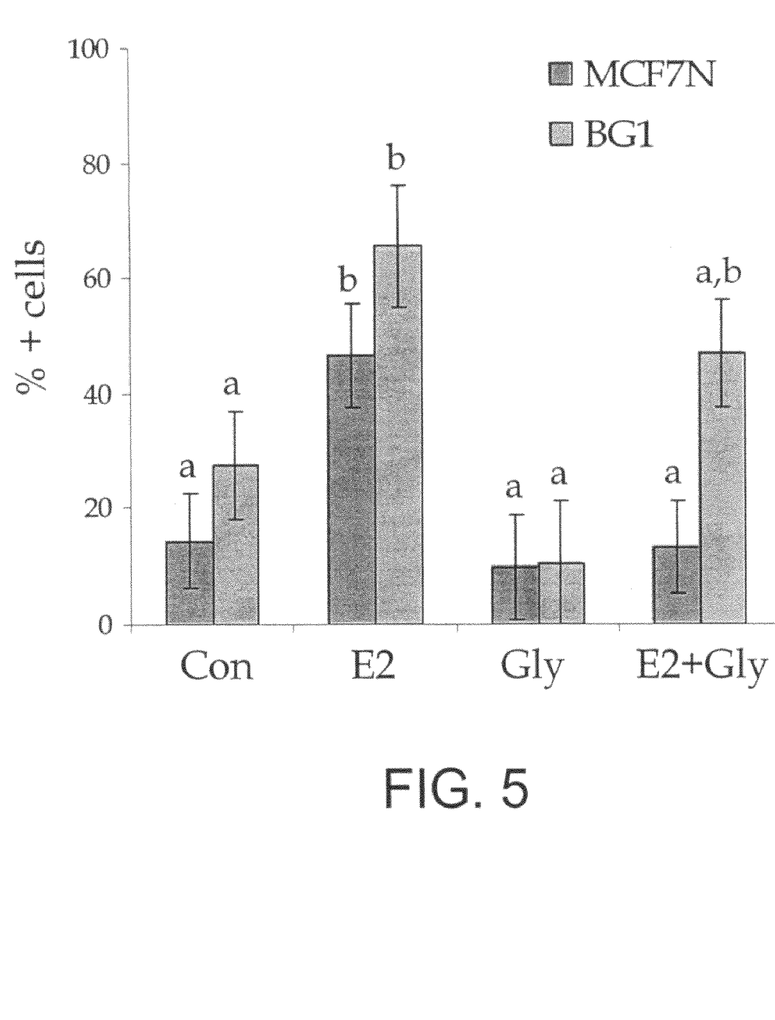
FIG. 5 depicts progesterone receptor (PR) expression in MCF-7 and BG1 tumor explants, as determined by immunohistochemistry. E2 treatment significantly increased PR compared to control, while glyceollin-alone had no effect. PR in E2+glyceollin was significantly lower than for E2-alone in MCF-7 cells and did not differ significantly from control treatment for either cell line. Treatments included-4-5 animals per group. Different letters indicate significant differences between groups ($p<0.05$ by ANOVA).

Progesterone receptor expression is an estrogen-sensitive marker driven by ER transactivation. In this study we used PR immunostaining to evaluate (a) whether glyceollin treatment alone was stimulating the ER as an agonist and (b) whether glyceollin treatment with estradiol (E2) was antagonizing ER activation. E2 treatment significantly increased PR expression (C vs E2, p<0.05) while glyceollin alone did not (C vs Gly, p=0.92) (FIG. 5). Treatment with glyceollins, when given with E2, completely blocked E2 effects on PR expression in MCF-7 tumors (E2 vs E2+Gly, p<0.05) and partially antagonized E2 effects in BG1 tumors (C vs E2+Gly, p=0.16).

Example 7

Uterine Morphology

Uteri were removed at necropsy, weighed, fixed in 70% ethanol, sectioned transversely through each uterine horn, embedded in paraffin, and stained with hematoxylin and eosin by routine procedures. Slides were photographed at 2× and 40× magnification using a Nikon CoolPix E995 digital camera (Melville, N.Y.). Uterine area, thickness, and epithelial height were measured from digital images using public domain software (NIH Image v1.62; available at http://rsb.info.nih.gov/nihimage/download.html). For epithelial height, three separate measurements were taken and the average was used for each animal. H&E-stained uteri were evaluated qualitatively for histologic changes.

Data for epithelial height were subjected to one-way analysis of variance. All variables were evaluated for their distribution and equality of variances between groups. A two-tailed significance level of 0.05 was chosen for all comparisons. Analyses were done using the SAS statistical package (version 6.08; SAS Institute, Cary, N.C.).

Figure 6:
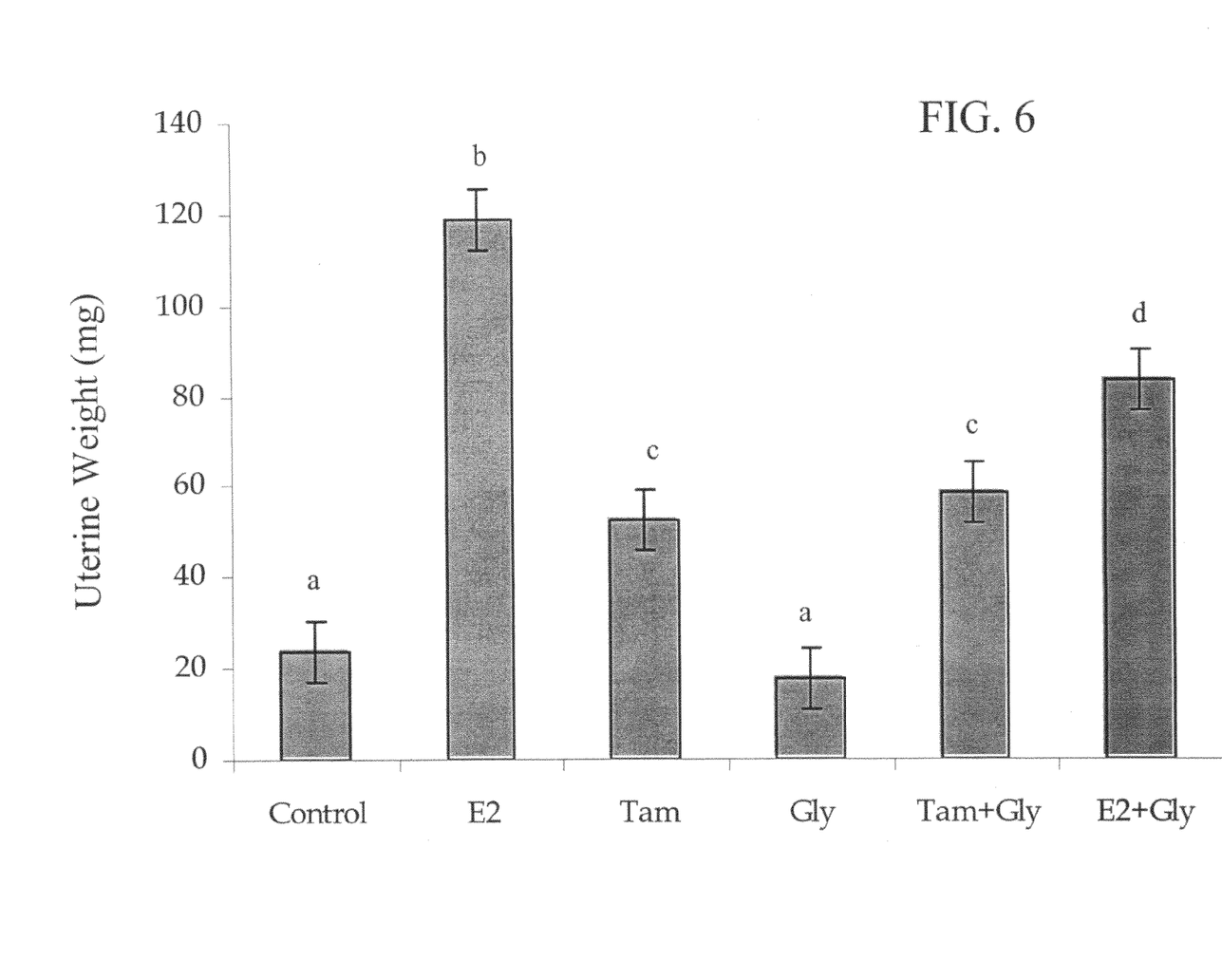
FIG. 6 depicts the effect of E2, glyceollin, tamoxifen, and tamoxifen with glyceollin, and E2 with glyceollin on uterine weights.
Figure 7:
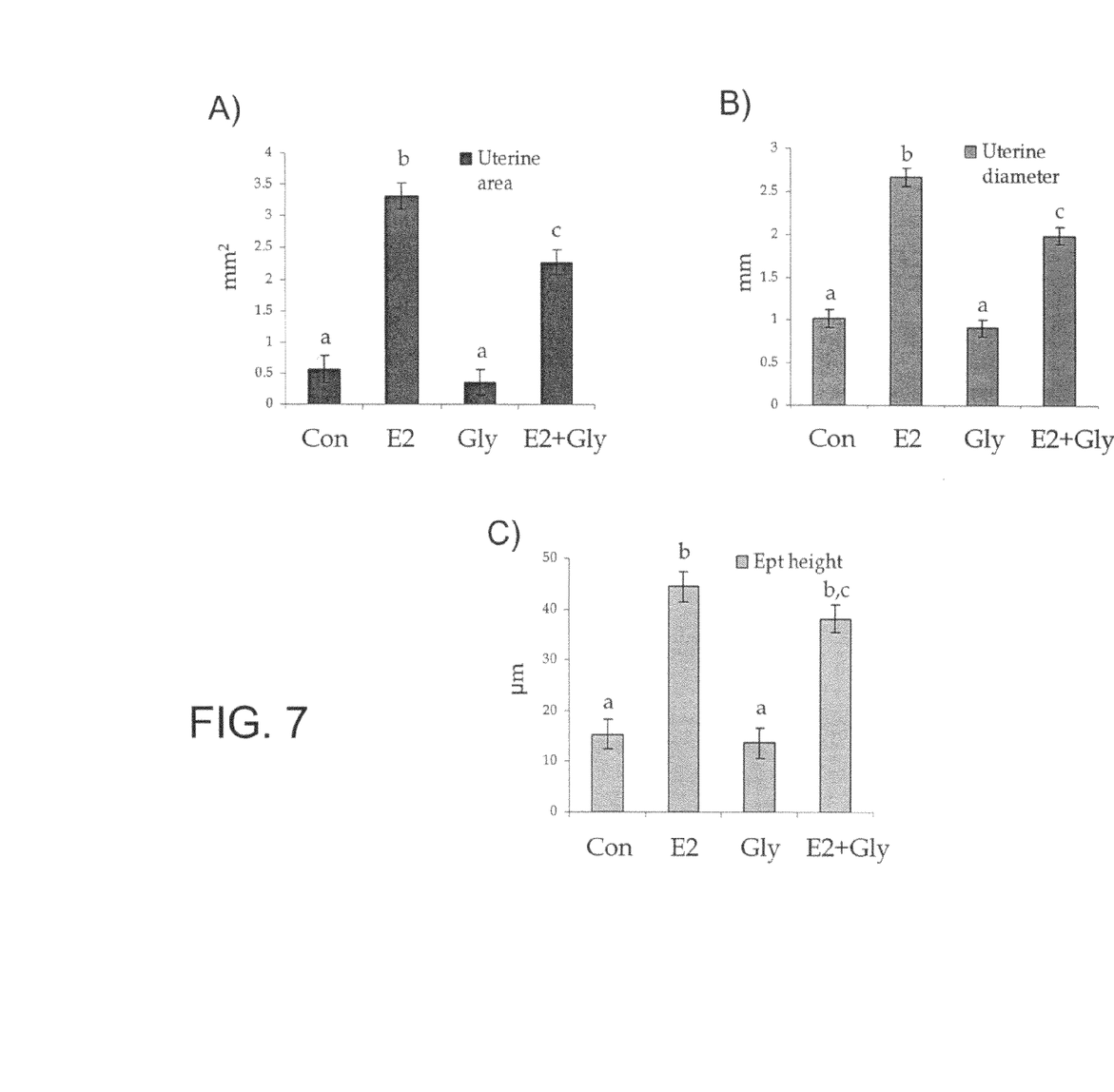
Figure 8:
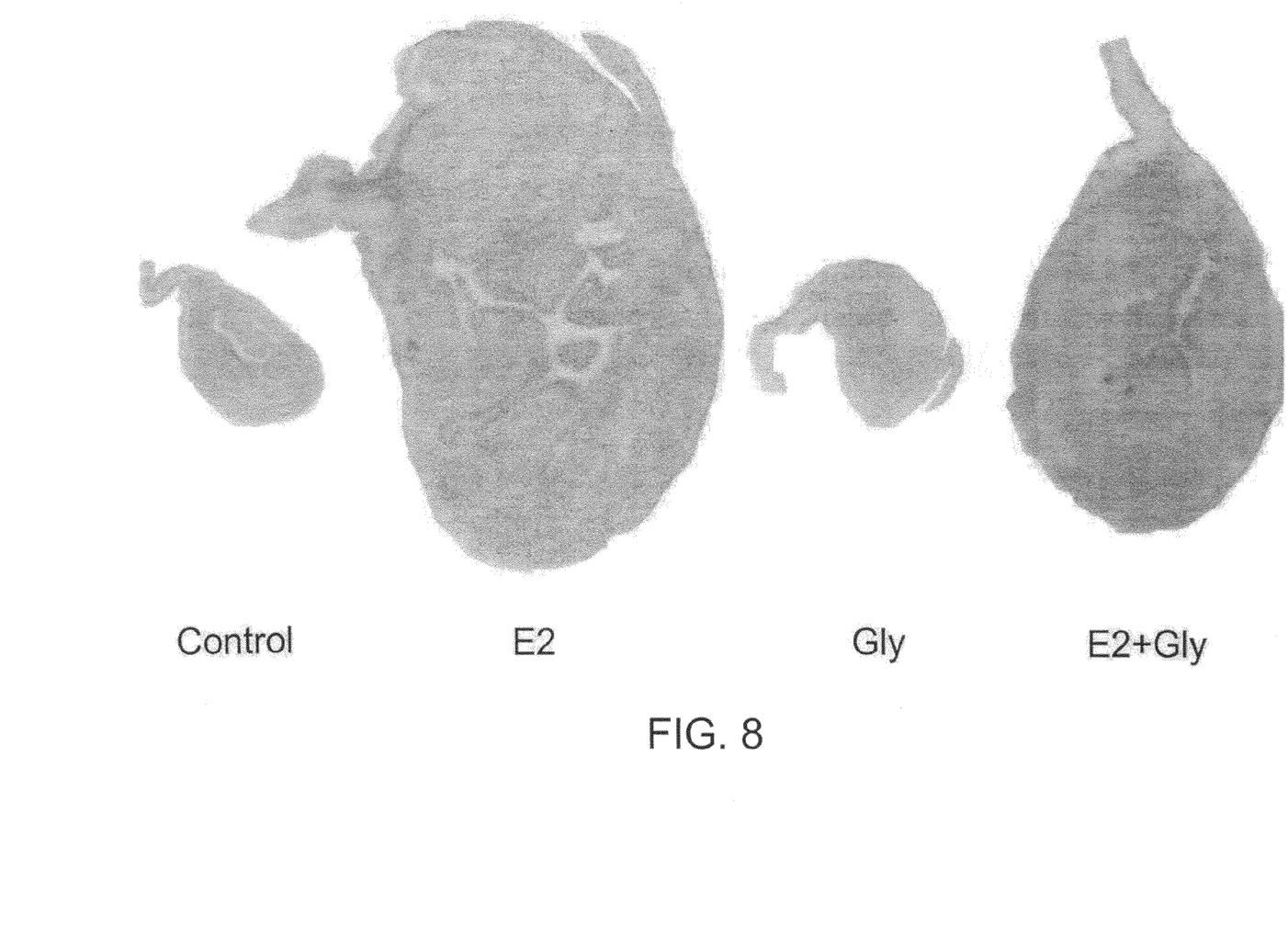
FIG. 8 shows sections of mouse uteri evaluated to assess whether glyceollin treatment had estrogen-like effects on other reproductive tissues. On histology, uteri from control and glyceollin-treated animals were diffusely atrophic and could not be distinguished morphologically.

Mouse uteri were evaluated to assess whether glyceollin treatment had estrogen-like effects on other reproductive tissues. Uterine weights are given in FIG. 6. Glyceollin combined with E2 did not significantly decrease the uterine weight below the level measure for E2 alone. Uterine area, uterine diameter, and epithelial height were significantly increased by E2 (C vs E2, p<0.0001), but not glyceollin treatment (FIG. 7). Glyceollin treatment in turn partially antagonized E2 effects on the uterus, significantly reducing uterine area and diameter (E2 vs E2+Gly, p<0.01). On histology, uteri from control and glyceollin-treated animals were diffusely atrophic and could not be distinguished morphologically (FIG. 8). Superficial epithelial cells were predominantly cuboidal with round to oval nuclei, while stromal cells were densely packed with scant cytoplasm. Uteri from E2-treated mice were markedly larger with epithelial pseudostratification, stromal edema and hyperplasia, and increased numbers of endometrial glands.

Data Analysis: Data for MCF-7N and BG-1 tumor size were analyzed separately using repeated measures two-way ANOVA with treatment and time as independent factors (SigmaStat 3.1). Data failed normality testing and so were rank transformed before analysis. Power for each of these comparisons (treatment, trial day, treatment×trial day) was 1.0. Post-hoc multiple pairwise comparisons testing using the Holm-Sidak method followed. Overall statistical significance level was set at p=0.05, but critical p levels for individual pairwise comparisons were adjusted for the number of comparisons. Tumor sizes are reported as treatment group means±SEM.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A method of treating, minimizing, or reducing cancer or tumor growth in a female individual having breast cancer or ovarian cancer, said method comprising administering to the individual a composition comprising isolated or synthetic glyceollin in an amount effective for the therapeutic treatment of breast cancer and ovarian cancer and determining the development or growth of breast cancer or ovarian cancer has been inhibited, minimized, or reversed.

* * * * *